(12) United States Patent
Gutman et al.

(10) Patent No.: US 6,593,486 B2
(45) Date of Patent: *Jul. 15, 2003

(54) PROCESS FOR MAKING CYANOMETHYL ESTER PRECURSORS OF FLECAINIDE

(75) Inventors: Arie L. Gutman, Haifa (IL); Genady Nisnevich, Nesher (IL); Eleonora Shkolnik, Nesher (IL); Igor Zaltzman, Haifa (IL); Boris Tishin, Haifa (IL)

(73) Assignee: Par Pharmaceutical, Inc., Spring Valley, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/911,366

(22) Filed: Jul. 23, 2001

(65) Prior Publication Data

US 2002/0133013 A1 Sep. 19, 2002

Related U.S. Application Data

(63) Continuation of application No. 09/422,931, filed as application No. PCT/IL98/00187 on Apr. 20, 1998, now Pat. No. 6,316,627, and a continuation-in-part of application No. PCT/IL98/00315, filed on Jul. 7, 1998.

(30) Foreign Application Priority Data

Apr. 21, 1997 (IL) ................................................ 120715
Jul. 11, 1997 (IL) ................................................ 121288

(51) Int. Cl.[7] ...................... C07C 253/00; C07C 255/14
(52) U.S. Cl. ........................ 558/311; 558/399; 558/308
(58) Field of Search ................................ 558/311, 308, 558/399

(56) References Cited

U.S. PATENT DOCUMENTS

| | | | |
|---|---|---|---|
| 2,045,760 A | | 6/1936 | Diescher et al. |
| 4,952,574 A | | 8/1990 | Banitt |
| 6,316,627 B1 | * | 11/2001 | Gutman et al. ............. 546/233 |

FOREIGN PATENT DOCUMENTS

| | | |
|---|---|---|
| EP | 0 455 545 | 6/1991 |
| GB | 2045760 | 11/1980 |

OTHER PUBLICATIONS

Abstract of JP 0539240 (Feb. 19, 1993).
Banitt et al., "Antiarrhythmics. N–(Aminoalkylene) trifluoroethoxybenzamides and N–(Aminoalkylene) trifluoroethoxynaphthamides," *J. Med Chem.*, 18:1130–1134 (1975).
Banitt et al., "Antiarrhythmics. 2. Synthesis and Antiarrhythmic Activity of N–(Piperidylalkyl) trifluoroethoxybenzamides", *J. Med. Chem.*, 20:821–826 (1977).
Barton et al., "Comprehensive Organic Chemistry. The Synthesis and Reactions of Organic Compounds," *Pergamon Press*, 1:583–584.
Buyle et al., "Sur les esters actives I. Aminolyste des derives acyles des oximes et amidoximes," *Helvetica Chimica Acta* 47:2444–2448 (1964).
Chemical Abstract 114:122069, Spanish Patent ES 2 007 802 to Rubio Zurito et al. of Jul. 1, 1989.
Flecainide, Merick Index, 12th Edition, 4136:694 (1996).
Lindley, "Tetrahedron Report No. 163. Copper Assisted Nucleophilic Substitution of Aryl Halogen," *Pergamon Press ltd.*, 40:1433–456.
March, "Advanced Organic Chemistry. Reactions, Mechanisms and Structure," *A Wiley–Interscience Publication*, 4th Edition, pp. 648–655 and 562–565 (1992).
Schwayzer et al., "Uber aktivierte Ester. I. Aktivierte Ester der Hippursaure und ihre Umesetzungen mit Benzylamin," *Helvetica Chimica Acta* 38:68–79 (1955).
Schwayzer et al., "Uber aktivierte Ester. II. Synthese aktivierter Ester von Aminosaure–Derivaten," *Helvetica Chimica Acta* 38:80–83 (1955).
Schwayzer et al., "Uber aktivierte Ester. III. Umsetzungen aktivierte Ester von Aminosauer–und Peptid–Derivaten mit Aminen und Aminosauereestern," *Helvetica Chimica Acta* 38:82–91 (1955).
Wrobel et al., "Syntheses of Tolrestat Analogues Containing Additional Substitutents in the Ring and their Evaluation as Aldose Reductase Inhibitors. Identification of Potent, Orally Active 2–Fluoro Derivatives," *J. Med. Chem.* 34:2504–2520 (1991).

* cited by examiner

*Primary Examiner*—Charanjit S. Aulakh
(74) *Attorney, Agent, or Firm*—Needle & Rosenberg, P.C.

(57) ABSTRACT

This application relates to a process for the preparation of the cyanomethyl ester

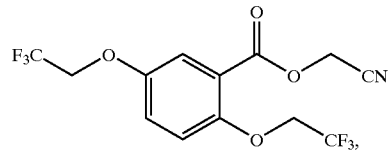

which comprises reacting 2,5-bis(2,2,2-trifluoroethoxy) benzoic acid or a salt thereof, with a haloacetonitrile of the formula $XCH_2CN$ wherein X is Cl, Br, or I.

3 Claims, No Drawings

PROCESS FOR MAKING CYANOMETHYL ESTER PRECURSORS OF FLECAINIDE

CROSS REFERENCE TO RELATED APPLICATIONS

This application is a CONTINUATION of, and claims the benefit of, application Ser. No. 09/422,931, filed Oct. 21, 1999, not U.S. Pat. No. 6,316,629, was a U.S. National Phase filing under 35 U.S.C. §371 and continuation in part of prior application numbers PCT/IL98/00187 filed on Apr. 20, 1998 and PCT/IL98/00315 filed Jul. 7, 1998, which claimed the benefit under 35 U.S.C. §119 of the filing date of Application No. 120715 in Israel filed Apr. 21, 1997 and Application No. 121288 in Israel filed Jul. 11, 1997, all of which applications are hereby incorporated herein in their entirety by reference.

FIELD OF THE INVENTION

The present invention relates to a novel process for the preparation of Flecainide or a precursor thereof, to a novel intermediate used in this process and its preparation.

BACKGROUND OF THE INVENTION

Flecainide (2,5-bis(2,2,2-trifluoroethoxy-N-(2-piperidylmethyl)benzamide is an effective antiarrythmic drug that acts on the cell membrane to reduce fast inward depolarization current.

One prior art method for preparing Flecainide [IV], disclosed in British Patent Application No. 2,045,760, starts from 2,5-bis(2,2,2-trifluoroethoxy)benzoic acid [III].

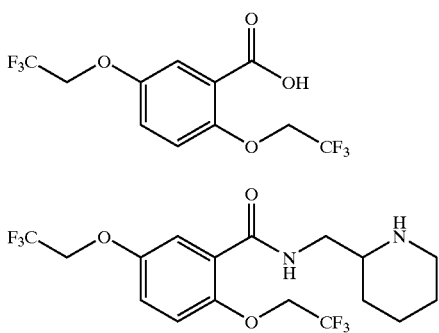

Compound [III] is prepared by a multi-stage process, comprising the conversion of 1,4-dibromobenzene or hydroquinone to 1,4-bis(2,2,2-trifluoroethoxy)benzene, which is acetylated to form 2,5-bis(2,2,2-trifluoroethoxy) acetophenone. The acetophenone is then oxidized to form the corresponding benzoic acid derivative, which is then converted to its acid chloride and reacted either with 2-(aminomethyl)piperidine to form the Flecainide product in one step or with 2-(aminomethyl)pyridine, followed by catalytic hydrogenation of the pyridine ring, to form Flecainide in two steps.

The one step process has a serious disadvantage in that the acid chloride reacts non-selectively with both nitrogen atoms of the 2-(aminomethyl)piperidine, resulting in a mixture of the two acylated isomers. This is the main reason why the two-step process via the pyridine intermediate is commercially preferred. A further disadvantage is due to the fact that the acid chloride intermediate disclosed in GB 2,045,760A is a liquid which cannot be stored for long periods of time, but must be used immediately after it is prepared.

Trifluoroethoxybenzoic acids of the formula [I] are useful intermediates in the pharmaceutical industry.

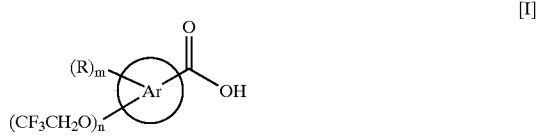

These compounds can be obtained by the reaction of hydroxybenzoic acids of the general formula [V] with 2,2,2-trifluoroethyl triflate [VI] according to Scheme 1 (Banitt, E. H. et al., J. Med. Chem. 18:1130 (1975)).

Scheme 1

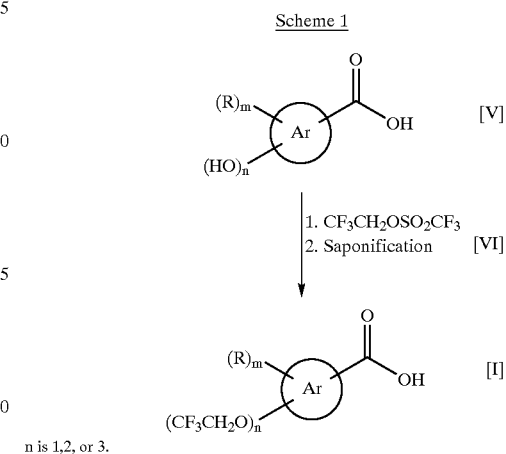

n is 1,2, or 3.

This method requires the use of trifluoroethyl triflate [VI] which is costly and not easily available commercially.

Another method (GB2045760A) involves the oxidation of the acetyl group of trifluoroethoxyacetophenones with hypochlorite as shown in Scheme 2. However, partial halogenation of the benzene ring may occur in this process, thus making it difficult for production of the (2,2,2-trifluoroethoxy)benzoic acids [I] as pharmaceutical precursors.

Scheme 2

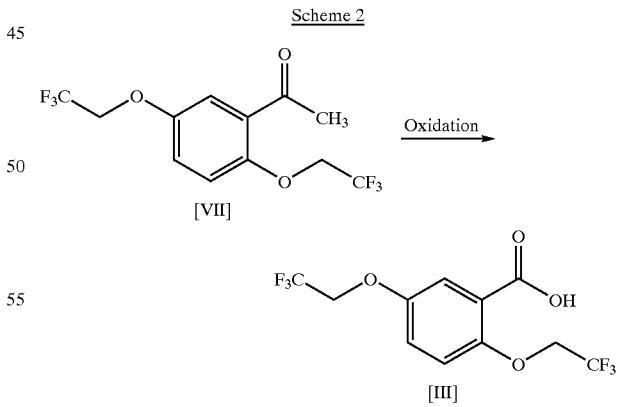

There is only one reported example of copper assisted fluoroalkoxy-de-halogenation of a 2-bromo-1-naphthalenecarboxylic acid derivative (Wrobel J. et al., J. Med. Chem. 34, 2504 (1991)). This example is very specific since it describes the de-halogenation of an active halogen, i.e. bromine, which is also located in a highly activated ortho position to a carboxylic group.

SUMMARY OF THE INVENTION

It is an object of the invention to provide a novel process for the preparation of trifluoroethoxy benzoic acid derivatives, in particular Flecainide, and their pharmaceutically acceptable salts, which is free of the above-mentioned disadvantages, starting with commercially available halobenzoic acids and involving the use of simple reagents and low cost solvents, to afford high overall yield of the product.

The above object is achieved in accordance with the present invention which, in one aspect thereof, provides a process for preparing a compound of formula (A):

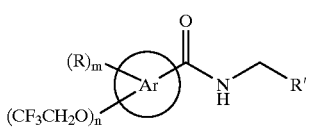

(A)

wherein
Ar represents a benzene ring;
R is hydrogen or a substituent selected from alkyl, alkoxy, alkylthio, halogen, haloalkyl, haloalkoxy, haloalkylthio, phenyl, phenoxy, benzyloxy, N-substituted or N,N-disubstituted amino groups, nitro, alkoxycarbonyl, cyano, carboxyl and when m>1 the R substituents may be the same or different;
R' is a 2-piperidyl or 2-pyridyl radical,
n is 1, 2 or 3;
m is 0, 1, 2, 3 or 4; where n+m≦5; and
pharmaceutically acceptable salts thereof, which process comprises the steps of:
a) reacting a halobenzoic acid or a salt thereof of the formula [II]

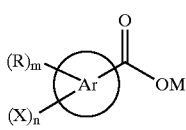

[II]

wherein
Ar, R, n and m are as defined above;
M is hydrogen or a metal, ammonium or phosphonium cation; and
X is Cl, Br or I, and when n>1 the X substituents may be the same or different;
with 2,2,2-trifluoroethanol in the presence of a strong base and a copper containing material, if desired followed by acidification to obtain a compound of formula [I]

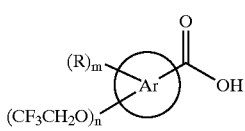

[I]

wherein Ar, R, m and n are as defined above, and
b) converting the product obtained in step a) above into the compound of formula (A) or a pharmaceutically acceptable salt thereof.

According to a specific embodiment, the present invention provides a process for the preparation of a compound of formula (A'):

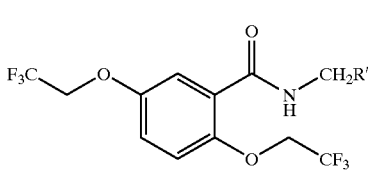

(A')

wherein R' is a 2-piperidyl or 2-pyridyl radical, and pharmaceutically acceptable salts thereof.

Step b) above may be carried out by known procedures, such as those described in GB 2,045,760A or in Chem. Abs. 114:122069. Alternatively, according to a preferred embodiment, the present invention provides a novel process for step b). This novel process comprises:
(i) reacting a compound of formula [I] or a salt thereof, with a haloacetonitrile of the formula $XCH_2CN$, where X is Cl, Br or I, if necessary in the presence of an inorganic or organic base, to form the cyanomethyl ester of the formula:

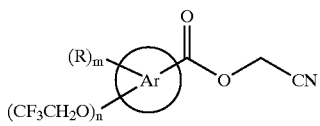

(ii) reacting the cyanomethyl ester with an amine of the formula $R'CH_2NH_2$ where R' is as defined above and, if desired,
(iii) converting the compound of the formula (A) into a pharmaceutically acceptable salt thereof.

Preferably, the halobenzoic acid in step a) is a compound of formula [XVII] or a salt thereof and the product of step a) is (2,2,2-trifluoroethoxy)-benzoic acid [III] or a salt thereof

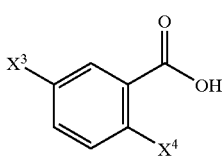

[XVII]

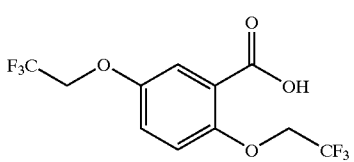

[III]

wherein:
$X^3$ is Br or I, $X^4$ is Cl, Br or I, or one of $X^3$ and $X^4$ may also be $CF_3CH_2O$—. (2,2,2-Trifluoroethoxy)benzoic acid [III] or a salt thereof may be converted in step b) into a compound of the formula (A') either by known methods or by the novel process of the present invention, which particularly comprises of:
(i) reacting 2,5-bis(2,2,2-trifluoroethoxy)benzoic acid [III] or a salt thereof, with a haloacetonitrile of the formula $XCH_2CN$, where X is Cl, Br or I, if necessary in the presence of an inorganic or organic base, to form the cyanomethyl ester of 2,5-bis(2,2,2-trifluoroethoxy) benzoic acid of the formula

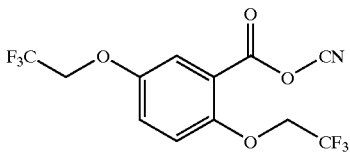

ii) reacting the cyanomethyl ester with an amine of the formula R'CH$_2$NH$_2$ where R' is as defined above and, if desired, iii) converting the resulting product of the formula (A')

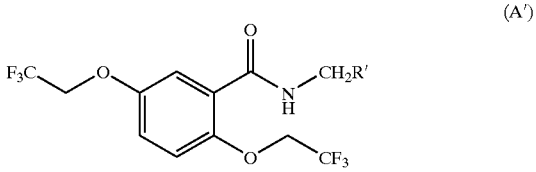

into a pharmaceutically acceptable salt thereof. A' represents Flecainide when R' is 2-piperidyl.

In accordance with another aspect of this invention, there is provided the novel cyanomethyl ester of 2,5-bis(2,2,2-trifuoroethoxy)benzoic acid having the formula above. The novel intermediate of the present invention is a stable, solid compound, obtainable in high yield, which can be easily purified by crystallization and stored for long periods of time.

DETAILED DESCRIPTION OF THE INVENTION (2,2,2-Trifluoroethoxy)benzoic acids [I] or salts thereof obtained in step a) of the process of the present invention may contain one or more 2,2,2-trifluoroethoxy groups. Additionally, other substituents R as defined above may be present on the aromatic ring.

As defined herein, the term "halobenzoic acid" includes benzoic acids containing one or more halogen atoms and optionally additional substituents as defined for R above.

According to a preferred embodiment of the present invention, a chloro-, bromo- or iodo-benzoic acid is reacted with a metal trifluoroethoxide in the presence of copper iodide or bromide in an aprotic solvent. Such aprotic solvent may be a dipolar aprotic solvent or an N-containing heterocycle or mixtures thereof. Examples of dipolar aprotic solvents are N,N-dimethylformamide, N-methylpyrrolidone, N,N-dimethylacetamide, DMSO and hexamethylphosphoramide. N-containing heterocyclic solvents used in the present invention are pyridine, picolines, lutidines, collidines, methylethylpyridine (MEP), other substituted pyridines, quinoline and substituted quinolines.

The reaction is preferably carried out at a temperature in the range of from ambient temperature to 170° C.

In the process of the invention, preferably at least one mole of 2,2,2-trifluoroethanol is used per each halogen atom of the halobenzoic acid [II] which is desired to be replaced by a trifluoroethoxy group. However, a large molar excess of 2,2,2-trifluoroethanol can be used in which cases this reactant may also serve as a solvent. At least one mole of 2,2,2-trifluoroethanol per mole of the strong base should be used and the mole ratio of the copper containing compound to the halobenzoic acid [I] can be in the range of 0.01 to 2:1.

Suitable copper containing materials are for example: copper salts, copper oxides, metallic copper, copper alloys, etc.

Compounds of formula [I] are converted in step b) into a desired compound of formula (A) either by known procedures or by a novel process which constitutes a further aspect of the present invention.

According to one prior art method described in GB 2,045,760A, 1,4-bis(2,2,2-trifluoroethoxy)benzene is acetylated to form the corresponding acetophenone, which is then oxidized to the benzoic acid derivative. The benzoic acid derivative is converted into the acid chloride and reacted either with 2-(aminomethyl)piperidine to form the Flecainide product in one step~or with 2-(aminomethyl)pyridine, followed by catalytic hydrogenation of the pyridine ring, to form Flecainide in two steps.

According to another prior art method described in Chem. Abs. 114:122069, 2,5-bis(2,2,2-trifluoroethoxy)benzoic acid may be converted into the corresponding acid chloride, which is reacted with 2-azaindolizidine to give the heterocyclic amide [XX] as the HCl salt, which is selectively hydrogenated to Flecainide, followed by salification with glacial acetic acid.

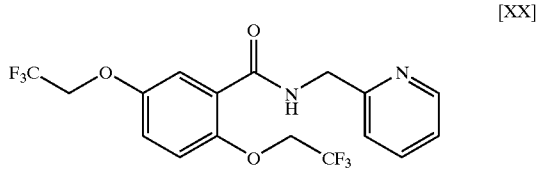

[XX]

Alternatively, as mentioned above, step b) is carried out by a novel process which comprises:

(i) reacting a compound of formula [I] or a salt thereof, with a haloacetonitrile of the formula XCH$_2$CN, where X is Cl, Br or I, if necessary in the presence of an inorganic or organic base, to form the cyanomethyl ester of the formula:

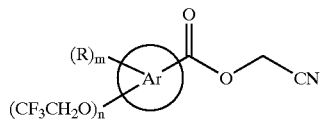

(ii) reacting the cyanomethyl ester with an amine of the formula R'CH$_2$NH$_2$ where R' is as defined above and, if desired, (iii) converting the compound of the formula (A) into a pharmaceutically acceptable salt thereof.

Preferably, (2,2,2-trifluoroethoxy)benzoic acid [III] or a salt thereof is obtained in step a) of the process of the invention from a halobenzoic acid of the formula [XVII] and is subsequently reacted with a haloacetonitrile of the formula XCH$_2$CN wherein X is Cl, Br or I, preferably Cl, in the presence of an inorganic or organic base, to give at the end of the process a compound of formula (A').

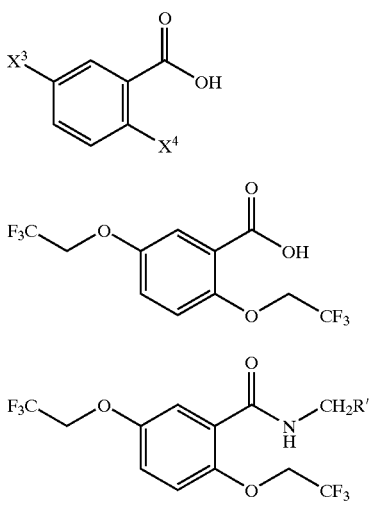

In the above formulae, $X^3$ is Br or I, $X^4$ is Cl, Br or I, or one of $X^3$ and $X^4$ may also be $CF_3CH_2O$—; R' is a 2-piperidyl or 2-pyridyl radical. When R' is 2-piperidyl, then the product is Flecainide or a salt thereof.

It was shown by Schwyzer et al. (Helvetica Chimica Acta, 1955, v. 38,69; 80;83) that cyanomethyl esters of aliphatic amino acids react selectively with primary amino groups. R. Buyle in Helvetica Chimica Acta, 1964, v. 47, p. 2444, showed that benzylamine reacts with cyanomethyl benzoate considerably slower than with cyanomethyl acetate. The present invention is based on the unexpected finding that 2,5-bis(2,2,2-trifluoroethoxy)benzoic acid activated by conversion to its cyanomethyl ester may react selectively and with high yield with primary amino groups of amines of the formula $RCH_2NH_2$ Thus, in step b) of the process, the cyanomethyl ester is reacted with an amine of the formula $RCH_2NH_2$ where R is as defined above, optionally in a suitable, inert solvent. Preferably, the reaction may be carried out by mixing together 2-(aminomethyl)piperidine with the cyanomethyl ester in a solvent such as 1,2-dimethoxyethane or ethyl acetate, to yield Flecainide (I) in a high yield.

The optional conversion of Flecainide into a pharmaceutically acceptable salt such as the acetate salt, is carried out by conventional methods.

The present invention will be described in more detail with the aid of the following non-limiting examples.

EXAMPLE 1

Synthesis of 2,5-bis(2,2,2-trifluoroethoxy)benzoic acid [III] from 5-bromo-2-chlorobenzoic acid [VIII] and 2,2,2-trifluoroethanol Scheme 3

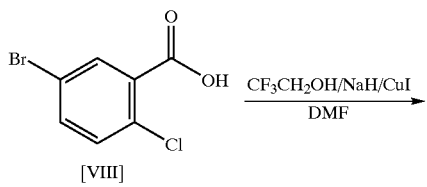

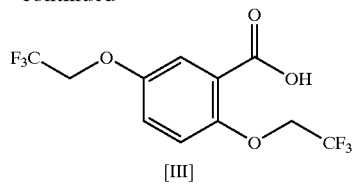

A 1 L round-bottomed flask equipped with a magnetic stirrer, a thermometer pocket, dropping funnel and a reflux condenser, was charged with 51.0 g of a 60% strength suspension of sodium hydride in mineral oil (equivalent to a total of 30.6 g (1.28 mole) of pure NaH and 570 mL of anhydrous N,N-dimethylformamide. The mixture was cooled to room temperature in an ice-water bath and 189.5 g (1.90 mole) of anhydrous 2,2,2-trifluoroethanol were added dropwise during 40 minutes.

The mixture was cooled to room temperature and 24.8 g (0.13 mole) of anhydrous copper iodide and 59.5 g (0.25 mole) of 5-bromo-2-chlorobenzoic acid were added. The black reaction mixture was heated to about 110–115° C. and kept at this temperature for 2 hours.

The reaction mixture was cooled to room temperature and poured into a mixture of crushed ice (3 kg) and conc. hydrochloric acid (0.78 L). The mixture was vigorously stirred for 1 hour, the black precipitate was filtered off and washed at once with 200 mL of water. The obtained solid was suspended at room temperature in 1 L of 5% aqueous KOH under vigorous stirring for 15 min, followed by filtration through a Celite modified filter and washing with 100 mL of 5% aqueous KOH.

The transparent clear alkaline solution was thrice extracted with 150 mL of dichloromethane. The alkaline solution was added dropwise under vigorous stirring to mixture of 0.6 kg of ice and 0.2 L of conc. hydrochloric acid, at a temperature not higher than 0° C. and a pH 1. The mixture was stirred for 0.5 hours at these conditions. The obtained precipitate was filtered off, washed with water, collected and dried under vacuum to a constant weight. Yield: 64.7 g (81.4%) of crude 2,5-bis(2,2,2-trifluoroethoxy) benzoic acid, m.p. 116–118° C. After recrystallisation from an ethanol/water system, a product with m.p. 120–121° C. was obtained.

EXAMPLES 2 TO 6

Syntheses of (2,2,2-trifluoroethoxy)benzoic Acids of the General Formula [X] by Reacting Sodium 2, 2,2-trifluoroethoxide with Corresponding Halobenzoic Acids [IX] Identified in Table 1

The procedures set forth in Example 1 were followed with the exceptions apparent from Table 1. Sodium 2,2,2-trifluorethoxide was prepared in situ by the action of sodium hydride on 2,2,2-trifluoroethanol.

In the following examples N,N-dimethylformamide, N,N-dimethylacetamide or N-methylpyrrolidone were used as solvents. In example 5, the solvent was 2,4,6-collidine. CuX was selected from copper iodide or copper bromide. The synthesis is described in Scheme 4.

Phisico-chemical parameters of 2,2,2-trifluoroethyl esters obtained by esterification of the products of experiments 2,3,4 and 1 are identical to corresponding 2,2,2-trifluoroethyl-2,5-bis(2,2,2-trifluoroethoxy)benzoates known in the art.

Scheme 4

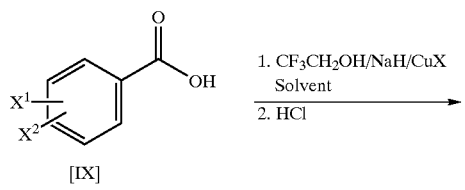

The results and the conditions are summarized in Table 1.

TABLE 1

| EXAMPLE NO. | $X^1$ | $X^2$ | $R^2$ | $R^3$ |
|---|---|---|---|---|
| 2 | 5-Br | 2-Br | 5-CF$_3$CH$_2$O | 2-CF$_3$CH$_2$O |
| 3 | 5-Br | 2-CF$_3$CH$_2$O | 5-CF$_3$CH$_2$O | 2-CF$_3$CH$_2$O |
| 4 | 5-I | 2-Cl | 5-CF$_3$CH$_2$O | 2-CF$_3$CH$_2$O |
| 5 | 5-Cl | 2-Cl | 5-Cl | 2-CF$_3$CH$_2$O |
| 6 | 5-NO$_2$ | 2-Cl | 5-NO$_2$ | 2-CF$_3$CH$_2$O |

EXAMPLE 7

Synthesis of Cyanomethyl Ester of 2,5-bis(2,2,2-trifluoroethoxy)benzoic Acid

A 1 L two-neck round-bottomed flask equipped with a heating mantle, a magnetic stirrer and a reflux condenser was charged under argon with a mixture of 62.8 g (197.4 mmole) of 2,5-bis(2,2,2,-trifluoroethoxy)benzoic acid, 22.4 g (296.1 mmole) of chloroacetonitrile and 29.9 g (296.1 mmole) of triethylamine in 250 mL ethyl acetate (EtOAc). The obtained mixture was refluxed for 3 hours. After cooling to 10° C., the mixture was filtered through a column containing 50 g of silica gel to remove the formed triethylammonium chloride. The filtrate was evaporated in vacuo and the product was dried under high vacuum for 1 hour at 50° C. The resulting colourless solidified oil was stirred with 200 mL of cold hexane to obtain white crystals. The crystals were filtered off, washed with cold hexane and dried at reduced pressure to give 60.0 g (85% yield) of cyanomethyl ester, having a purity of 99.5% (GC), m.p. 50–51° C., one spot on TLC.

1H NMR(CDCl$_3$) δ4.37 (4H,m); 4.93 (2H,s); 7.00 (1H,d); 7.17 (1H,dd); 7.44 (1H,d); HRMS:M$^+$357.0433, C$_{13}$H$_9$NO$_4$F$_6$.

EXAMPLE 8

Synthesis of Flecainide from the Cyanomethyl Ester of 2,5-bis (2,2,2-trifluoroethoxy)benzoic Acid and 2-(aminomethyl)piperidine

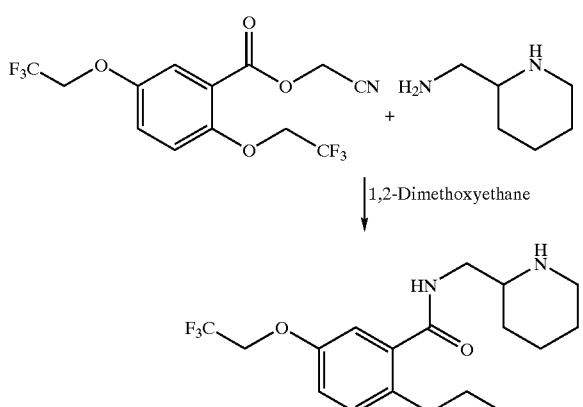

A mixture of the cyanomethyl ester prepared in Example 7 above (2.1 g, 5.9 mmole) and 2-(aminomethyl)piperidine (0.8 g, 7 mmole) in 1,2-dimethoxyethane (10 mL) was charged under argon into a 50 mL round-bottomed flask equipped with a magnetic stirrer. After stirring for 2.5 hours at room temperatures additional 2-(aminomethyl)piperidine (0.5 g, 4.7 mmole) was added. The mixture was stirred for additional 24 hours at room temperature. The solvent was removed in vacuo and the residue was dissolved in 10 mL methylene chloride. The obtained solution was extracted with water and the aqueous layer was extracted with additional 5 mL of methylene chloride. The combined organic layers were dried over sodium sulphate and evaporated under reduced pressure to give 1.9 g (77.6 yield) of white crystals of Flecainide, purity 99.1% (GC).

EXAMPLE 9

Synthesis of Flecainide Acetate

A mixture of the cyanomethyl ester prepared in Example 7 (95.0 g. 0.27 mole) and 2.(aminomethyl) piperidine (35.4 g. 0.31 mole) in 450 mL ethyl acetate (max water content: 0.05%) was charged under argon into a 1 L round-bottom flask equipped with a dropping funnel and magnetic stirrer. After stirring for 2 hours at room temperature, the additional amount (24.2 g. 0.21 mole) of 2-(aminomethyl)piperidine was added, and the mixture was stirred for an additional period of 12 hours at room temperature.

The solvent was evaporated under reduced pressure. The residue was dissolved in 250 mL. of dichloromethane. The obtained solution was treated with water (3×50 mL), dried wit anhydrous Na$_2$SO$_4$ filtered and concentrated under reduced pressure.

The residue was dissolved in boiling ethyl acetate (800 mL), and 30 g (0.5 mole) of glacial acetic acetic acid was added dropwise to the obtained solution. The mixture was stirred under reflux for an additional 10 minutes and allowed to cool to room temperature overnight, followed by cooling into an ice bath for 4 hours. The crystalline product was filtered off, washed with cooled to 0° C. ethyl acetate (2×100 mL) and dried at 50° C. under reduced pressure, to obtain 103.0 g (82% from theoretical yield) of Flecainide acetate, m.p. 147–148° C.

EXAMPLE 10

Synthesis of 2,5-bis(2,2,2-trifluoroethoxy)-N-(2-pyridylmethyl)-benzamide

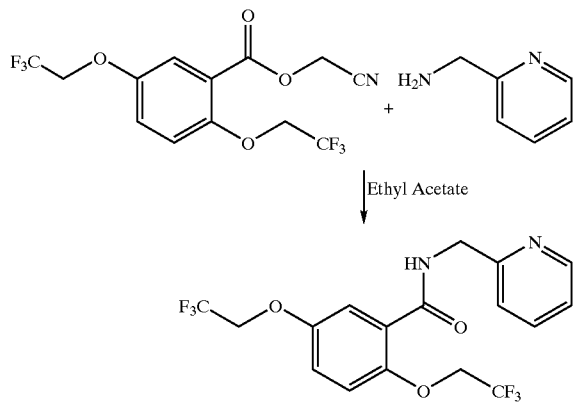

To a solution of 8.93 g (2.5 mmole) of the cyanomethyl ester prepared in Example 7 in 80 mL of ethyl acetate under argon, 2-(aminomethyl)pyridine (3.2 g, 3.0 mmole) were added with stirring and the mixture was refluxed for 4 hours. An additional 1 g of 2-(aminomethyl)pyridine was added and the mixture was refluxed for two more hours. The ethyl acetate was evaporated under reduced pressure, and the residue was passed through a 12 cm column containing silica gel with a mixture of methlylene chloride: hexane (1:1) as eluent. The column was washed with methylene chloride and the combined solutions were evaporated under reduced pressure. The residue was crystallized from $CH_2Cl_2$: hexane (1:2) to give 7 g (69% yield) of 2,5-bis(2,2,2-trifluoroethoxy)-N-(2-pyridylmethyl)benzamide m.p. 104–106° C., purity 99.8% (GC).

What is claimed is:

1. A process for the preparation of the cyanomethyl ester

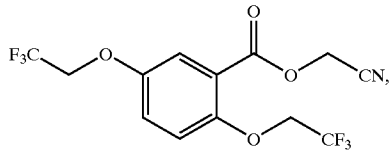

which comprises reacting 2,5-bis(2,2,2-trifluoroethoxy) benzoic acid or a salt thereof, with a haloacetonitrile of the formula $XCH_2CN$ wherein X is Cl, Br, or I.

2. The process according to claim 1, carried out in a suitable inert solvent.

3. The process of claim 1, carried out in the presence of an inorganic or organic base.

* * * * *